United States Patent [19]
Bakshi et al.

[11] Patent Number: 5,919,989
[45] Date of Patent: Jul. 6, 1999

[54] ETHERIFICATION PROCESS

[75] Inventors: Amarjit Bakshi; Thomas P. Hickey, both of Houston, Tex.

[73] Assignee: Catalytic Distillation Technologies, Pasadena, Tex.

[21] Appl. No.: 08/880,145

[22] Filed: Jun. 20, 1997

Related U.S. Application Data

[60] Provisional application No. 60/021,825, Jul. 16, 1996.
[51] Int. Cl.⁶ .................................................. C07C 41/00
[52] U.S. Cl. .................................................. 568/698
[58] Field of Search ............................................. 568/698

[56] References Cited

U.S. PATENT DOCUMENTS

| | | | |
|---|---|---|---|
| 3,629,478 | 12/1971 | Haunschild | 260/677 A |
| 3,634,534 | 1/1972 | Haunschild | 260/677 A |
| 3,634,535 | 1/1972 | Haunschild | 260/677 A |
| 4,232,177 | 11/1980 | Smith, Jr. | 585/324 |
| 4,307,254 | 12/1981 | Smith, Jr. | 568/697 |
| 4,336,407 | 6/1982 | Smith, Jr. | 568/697 |
| 4,504,687 | 3/1985 | Jones, Jr. | 568/697 |
| 4,950,803 | 8/1990 | Smith, Jr. et al. | 568/697 |
| 4,978,807 | 12/1990 | Smith, Jr. | 568/697 |
| 5,118,873 | 6/1992 | Smith, Jr. | 568/697 |
| 5,227,534 | 7/1993 | Harandi | 568/697 |
| 5,237,109 | 8/1993 | Patton et al. | 568/697 |
| 5,243,102 | 9/1993 | Marker et al. | 568/697 |
| 5,245,087 | 9/1993 | Zahn | 568/697 |

FOREIGN PATENT DOCUMENTS

WO 9601244  1/1996  WIPO ............... C07C 41/06

*Primary Examiner*—Paul J. Killos
*Assistant Examiner*—Jafar Parsa
*Attorney, Agent, or Firm*—Kenneth H. Johnson

[57] ABSTRACT

The overheads from an etherification distillation column reactor containing unreacted alcohol and isoolefin are fed to a finishing reactor and then a portion of the effluent from the finishing reactor is returned to the distillation column reactor.

15 Claims, 7 Drawing Sheets

ETHERIFICATION PROCESS

This application claims the priority benifit of Provisional application No. 60/021,825 filed Jul. 16, 1996.

BACKGROUND OF THE INVENTION

1. Field of the Invention

The present invention relates to the etherification of isoolefins, particularly $C_4$ and $C_5$ isoolefins, with an alcohol such as methanol to produce the corresponding tertiary ether. More particularly the invention relates to a process wherein a catalytic distillation process is used in the process and wherein the overheads from the distillation column reactor contain significant amounts of the alcohol and isoolefin. More particularly the invention relates to a process wherein the overheads are subjected to further reaction and the effluent from the reactor is fed back to the distillation column as reflux or stripper feed or a combination of both.

2. Related Information

The reaction of an alcohol and an olefin and concurrent separation of the reactants from the reaction products by fractional distillation has been practiced for some time. The process is variously described in U.S. Pat. Nos. 4,232,177; 4,307,254; 4,336,407; 4,504,687; 4,987,807; and 5,118,873, all commonly assigned herewith.

Briefly, the alcohol and isoolefin are fed to a distillation column reactor having a distillation reaction zone containing a suitable catalyst, such as an acid cation exchange resin, in the form of catalytic distillation structure, and also having a distillation zone containing inert distillation structure. As embodied in the etherification of $iC_4^=$'s and/or $iC_5^=$'s the olefin and an excess of methanol are first fed to a fixed bed reactor wherein most of the olefin is reacted to form the corresponding ether, methyl tertiary butyl ether (MTBE) or tertiary amyl methyl ether (TAME). The fixed bed reactor is operated at a given pressure such that the reaction mixture is at the boiling point, thereby removing the exothermic heat of reaction by vaporization of the mixture. The fixed bed reactor and process are described more completely in U.S. Pat. No. 4,950,803 which is hereby incorporated by reference.

The effluent from the fixed bed reactor is then fed to the distillation column reactor wherein the remainder of the $iC_4^=$'s or $iC_5^=$'s are usually converted to the ether and the methanol is separated from the ether which is withdrawn as bottoms. The $C_4$ or $C_5$ olefin stream generally contains only about 10 to 60 percent olefin, the remainder being inerts which are removed in the overheads from the distillation column reactor.

In some cases the distillation column reactor may be operated such that complete reaction of the isoolefin is not achieved for a particular reason and therefore there may be significant isoolefin in the overheads, that is, from 1 to 15 wt %, along with unreacted methanol.

SUMMARY OF THE INVENTION

Briefly, the present invention comprises feeding the overheads from an etherification distillation column reactor to a finishing reactor and then returning substantially all (preferably a portion either of the overheads from the distillation column reactor or the finishing reactor effluent is removed separately to prevent build up of unwanted or inert components in the system) or a portion of the effluent from the finishing reactor to the distillation column reactor.

More specifically the process comprises a process for the production of tertiary ethers comprising the steps of:

(a) feeding a primary alcohol and an isoalkene to a distillation column reactor in a feed zone;

(b) concurrently in said distillation column reactor (i) contacting the primary alcohol and isoalkene in the presence of an etherification catalyst configured as a catalytic distillation structure in a distillation reaction zone thereby reacting a portion of the primary alcohol with a portion of the isoalkene to produce a reaction mixture containing tertiary ether product and unreacted primary alcohol and isoalkene and (ii) distilling the reaction mixture to separate the tertiary ether product from the unreacted primary alcohol and unreacted isoalkene;

(c) withdrawing tertiary ether product from said distillation column reactor as bottoms;

(d) withdrawing unreacted primary alcohol and unreacted isoalkene from said distillation column reactor as overheads;

(e) feeding said overheads to a single pass fixed bed reactor containing an etherification catalyst to further react primary alcohol with isoalkene to produce an effluent containing additional tertiary ether; and (f) feeding a portion of the effluent from said single pass fixed bed reactor to said distillation column reactor.

DESCRIPTION OF THE PREFERRED EMBODIMENT

Figure 1:
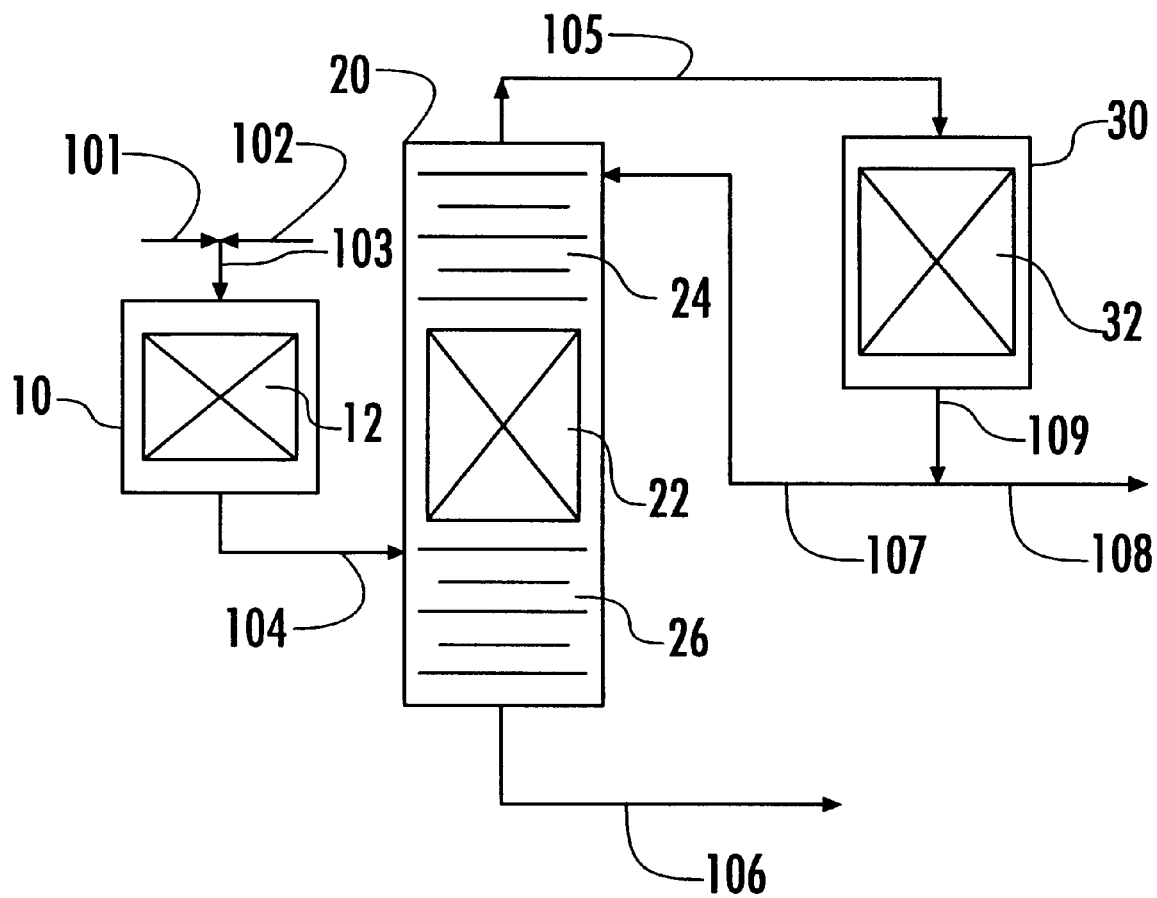
FIG. 1 is a flow diagram in schematic form of one embodiment of the present invention.

The preferred catalyst for the etherification is an acidic cation exchange resin such as Amberlyst manufactured by Rohm & Haas co.

A preferred structure for use in a catalytic distillation etherification is to dispose the resin beads in pockets of a cloth belt which is then wound into a spiral with demister wire which supports and separates the belts in the column. Such a system has been described in commonly assigned U.S. Pat. Nos. 4,215,011; 4,232,177; 4,242,530, 4,302,356; 4,307,254 4,336,407; 4,439,350 and 4,482,775. In addition U.S. Pat. Nos. 4,443,559 and 4,250,052 disclose a variety of catalyst structures for this use and are incorporated herein.

Typical conditions for the catalytic distillation MTBE reaction include catalyst bed temperatures of about 150–170° F., overhead pressures of about 90–110 psig and equivalent liquid hourly space velocities of about 1.0 to 2.0 $hr^{-1}$. Typically the methanol and $C_4$'s are first fed to a down flow guard bed reactor operated as a boiling point reactor wherein considerable etherification occurs prior to the distillation column reactor. The operation of the boiling point reactor for etherification is detailed in U.S. Pat. No. 4,950,803 which is herein incorporated by reference. The use of a boiling point reactor or any other preliminary reactor is optional. However such reactors are beneficial in that they serve as guard beds for the catalytic distillation structures in the reactor distillation column and also serve to reduce the amount of catalytic distillation structure required to achieve a given conversion of isoolefins.

Fixed bed etherifications are described in U.S. Pat. Nos. 4,475,005 and 4,336,407. Typically the conversion from a single pass fixed bed reactor is the equilibrium conversion of about 95% for the isobutene and about 70% for isoamylenes. However when a distillation column reactor is used the reaction is occurring concurrently with distillation, the initial reaction product is removed from the reaction zone as quickly as it is formed and thus cannot contribute to the reverse reaction (Le Chatelier's Principle). Thus higher than equilibrium conversions can be achieved.

The temperature in the column is determined by the boiling point of the liquid mixture present at any given pressure. The temperature in the lower portions of the column will reflect the constitution of the material in that portion of the column, which will be higher than the overhead; that is, at constant pressure a change in the temperature indicates a change in the composition in the column. To change the temperature the pressure is changed. Temperature control in the reaction zone is thus controlled by the pressure with the addition of heat (the reactions being exothermic) only causing more boil up. By increasing the pressure the temperature is increased, and vice versa.

Even though a distillation column reactor is used some of the isoolefin is unconverted and exits the column with the overheads. A finishing reactor is used to further react isoolefin in the overheads.

A first embodiment of the invention is shown in FIG. 1. Methanol and a $C_4$ or $C_5$ stream containing isoolefin (e.g. isobutene or isoamylenes) are fed to a single pass downflow reactor 10 via flow lines 101 and 102 respectively which are combined in flow line 103. The single pass reactor 10 contains a bed 12 of etherification catalyst such as Amberlyst 15. The reactor 10 is operated as a boiling point reactor as described in the above cited U.S. Pat. No. 4,950,803. Briefly the reactor 10 is operated such that the temperature of the reaction mixture is at the boiling point so that the exothermic heat of reaction is dissipated in the latent heat of vaporization of the mixture.

The effluent from the boiling point reactor 10 is fed via flow line 104 to a distillation column reactor 20 having a fixed bed 22 of the etherification catalyst (such as Amberlyst 15) in the form of a catalytic distillation structure. Above the catalyst bed 22 is a rectification section 24 having standard distillation structure and below the bed 22 is a stripping section 26 also containing standard distillation structure.

The ether product, being the highest boiling material, is removed from the distillation column reactor 20 as bottoms via flow line 106. The overheads, containing unreacted methanol and isoolefin along with light inerts such as normal butene and butanes or pentene and pentanes, are removed via flow line 105 and passed to a second single pass fixed bed reactor 30 also containing a bed 32 of the etherification catalyst. The operation of the second single pass reactor 30 is similar to the first reactor 10 except that due to the lower concentrations of reactants the exothermic heat of reaction may not need to be removed by boiling of the mixture. If necessary, the second single pass reactor 30 may also be operated as a boiling point reactor.

The effluent from the second single pass reactor 30 is removed via flow line 109 with a portion of the effluent being returned to the distillation column reactor 20 for separation of the product ether. Another portion is withdrawn via flow line 108 to prevent build up of inerts in the system. In the embodiment of FIG. 1 the effluent from the second single pass reactor 30 is fed back to the distillation column reactor 20 as reflux in the rectification section and as such would need to be cooled (not shown).

Figure 2:
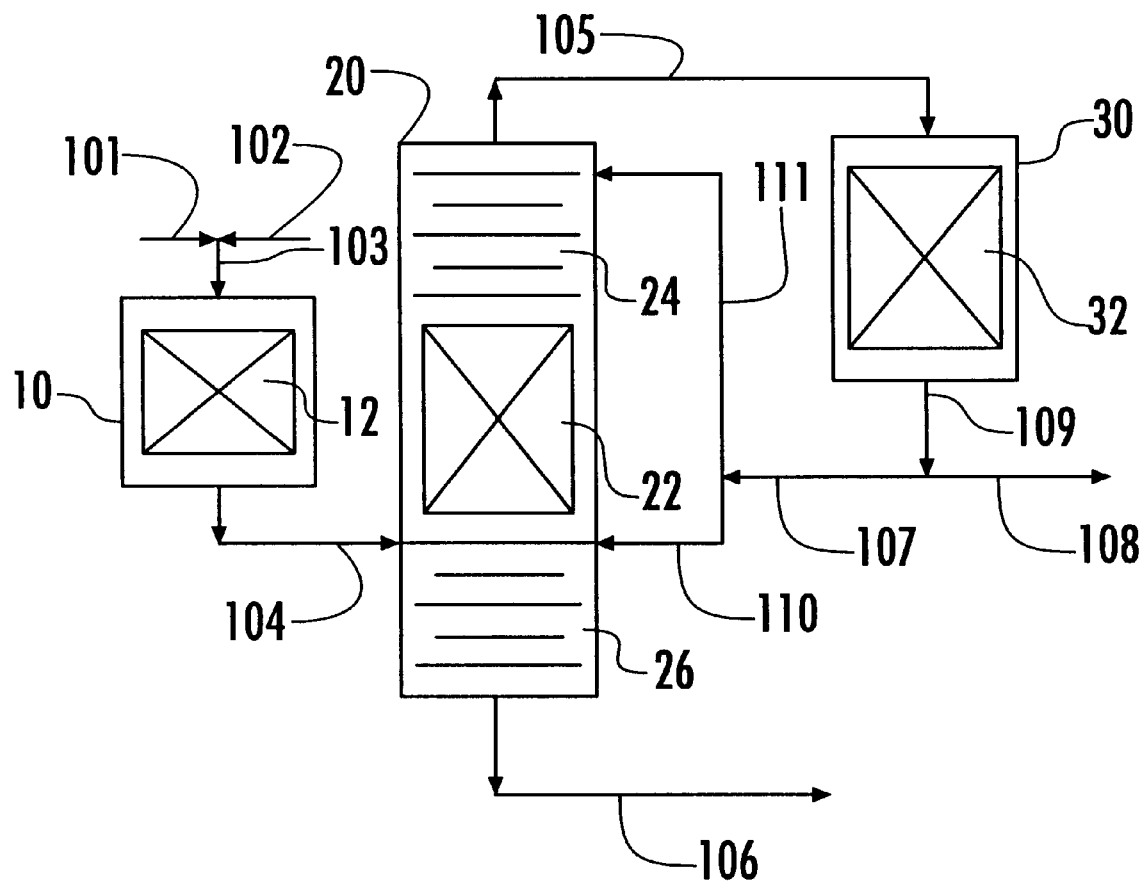
FIG. 2 is a flow diagram in schematic form of a second embodiment of the present invention.

A second embodiment of the invention is shown in FIG. 2. The only difference between the embodiments of FIG. 1 and FIG. 2 is that the effluent being returned to the distillation column reactor 20 via flow line 107 is split with a portion being returned as reflux via flow line 111 and a portion being fed directly to the stripping section via flow line 110. The remainder of the reference numerals are identical to those of FIG. 1.

Figure 3:
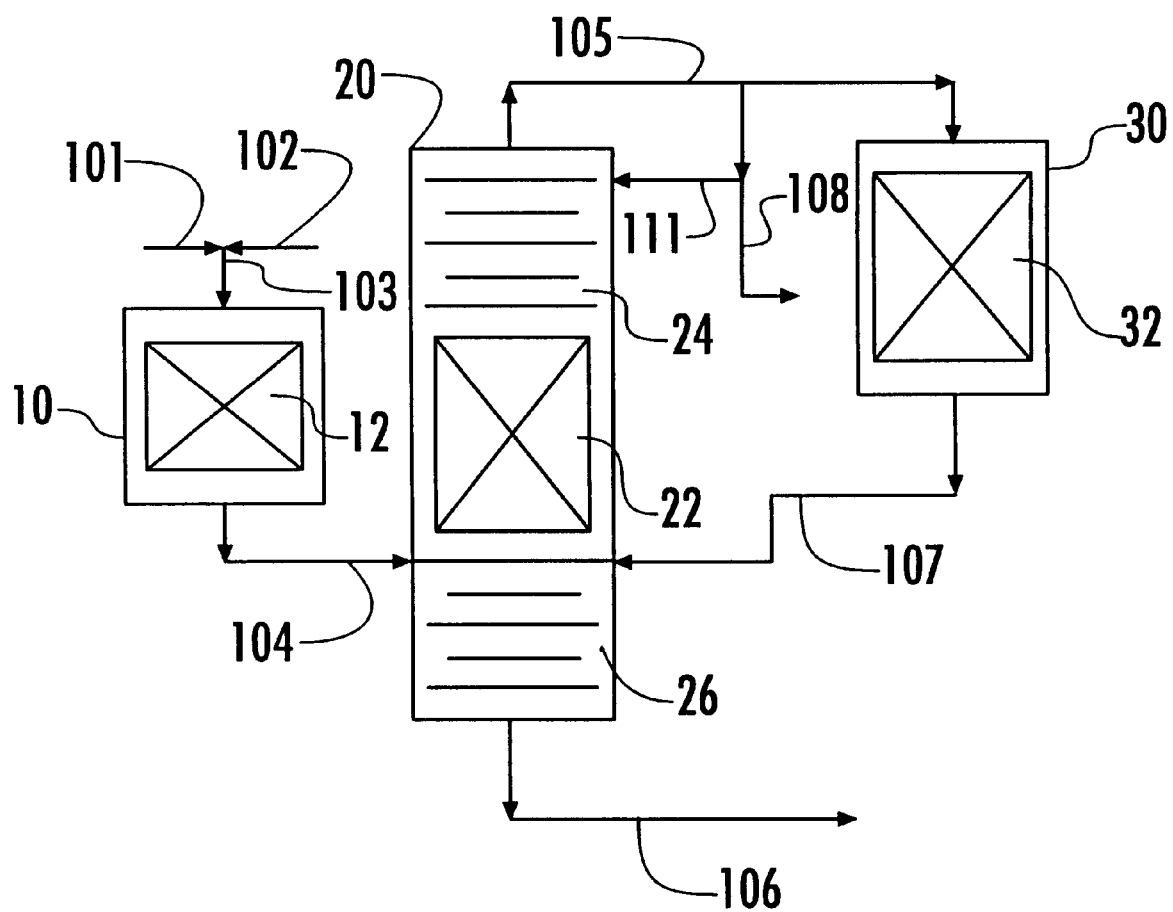
FIG. 3 is a flow diagram in schematic form of a third embodiment of the present invention.

A third embodiment is shown in FIG. 3 wherein a portion of the overheads from the distillation column reactor 20 is diverted back to the distillation column reactor 20 as reflux via flow line 111 with the slip stream for removal of inerts taken from this stream via flow line 108. The effluent from the second single pass fixed bed reactor 30 is fed back to the distillation column reactor 20 into the stripping section via flow line 107. With these changes the remaining reference numerals are the same as FIG. 1.

Figure 4:
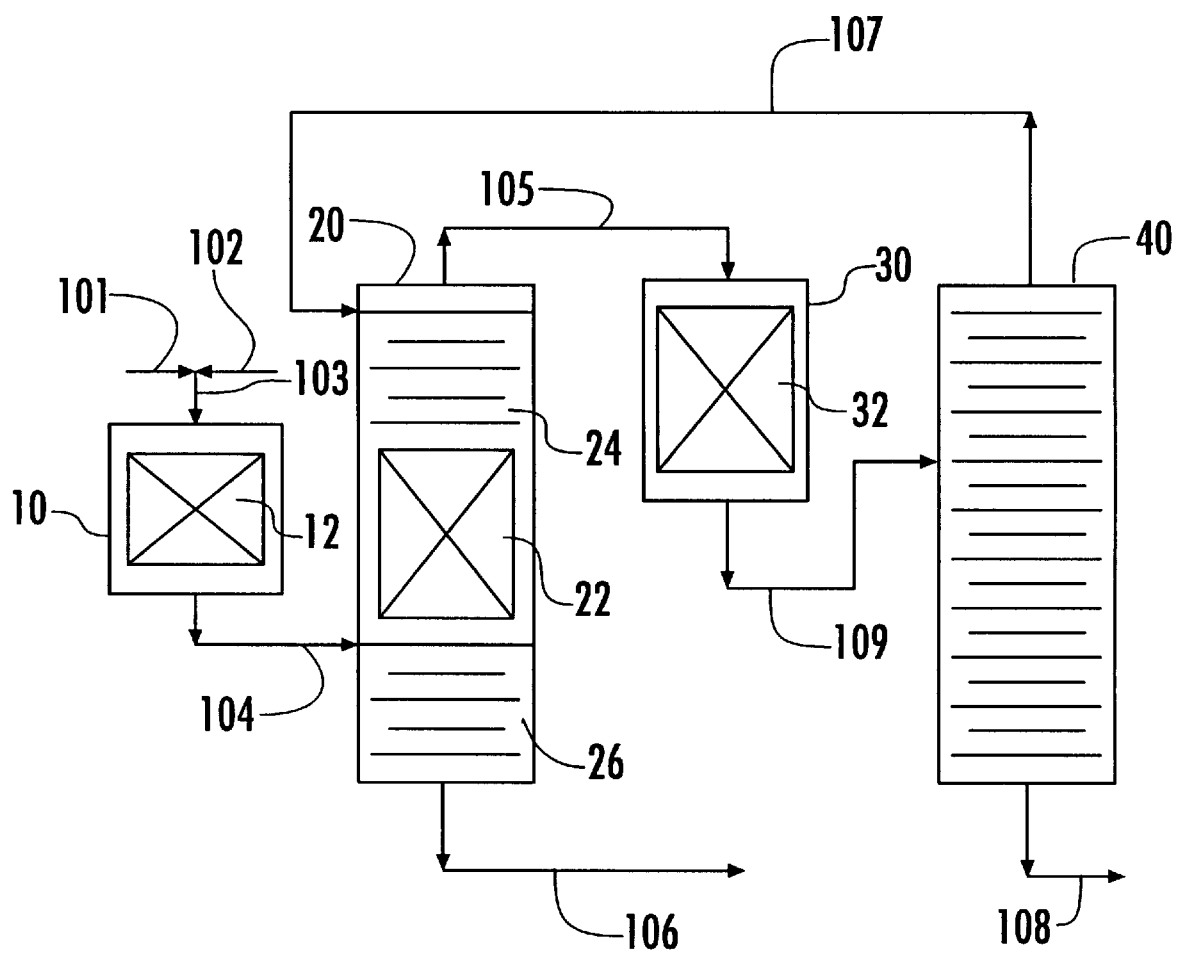
FIG. 4 is a flow diagram in schematic form of a fourth embodiment of the present invention.

In a fourth embodiment shown in FIG. 4 the effluent from the second single pass reactor 30 is fed to a standard distillation column 40 where the ether is separated from the other components and withdrawn as bottoms via flow line 108. The overheads from the standard distillation column 40 are split and a portion is returned as reflux in the distillation column reactor 20 via flow line 107 with another portion being purged as inerts via flow line 110. The remaining reference numerals in FIG. 4 are identical to FIG. 1.

Figure 5:
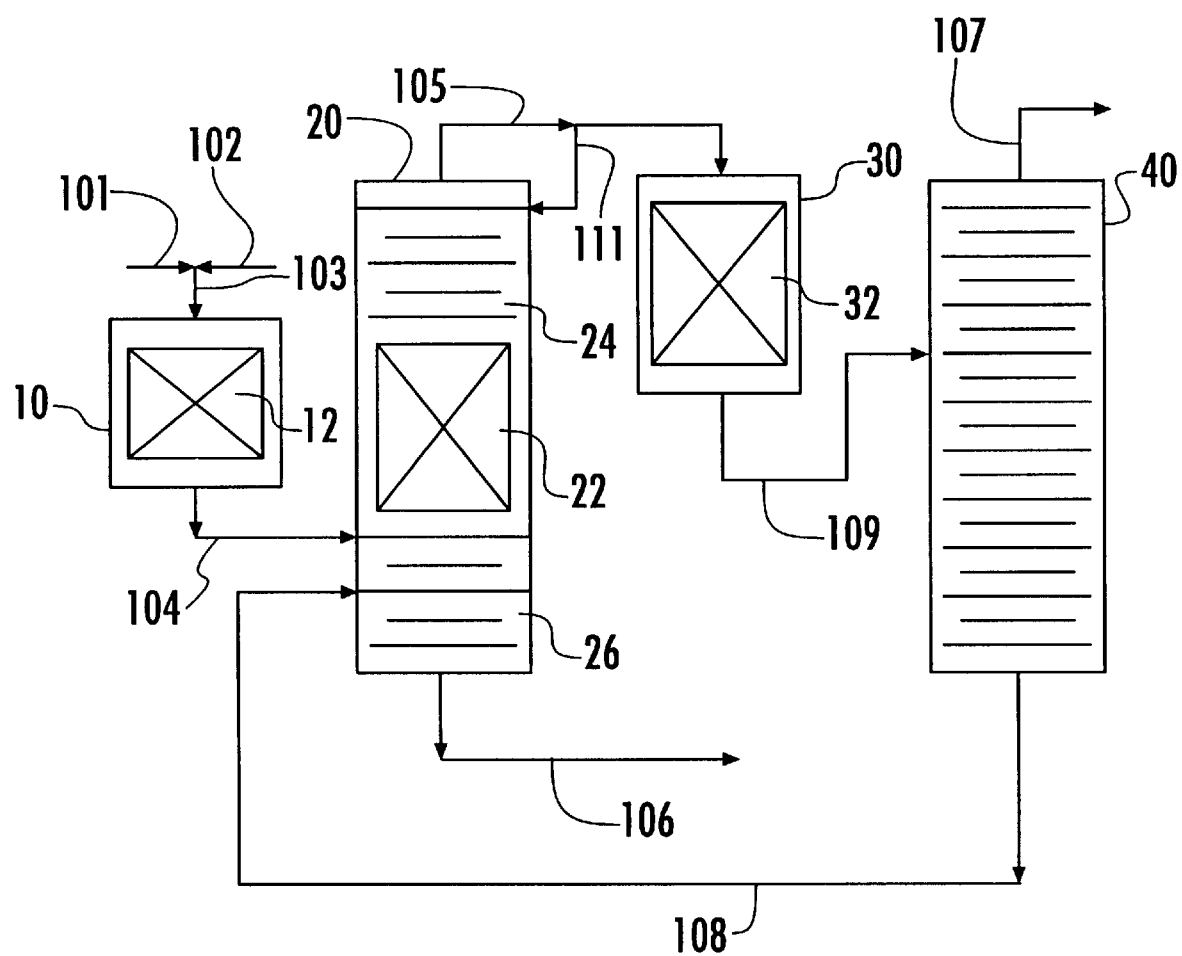
FIG. 5 is a flow diagram in schematic form of a fifth embodiment of the present invention.
Figure 7:
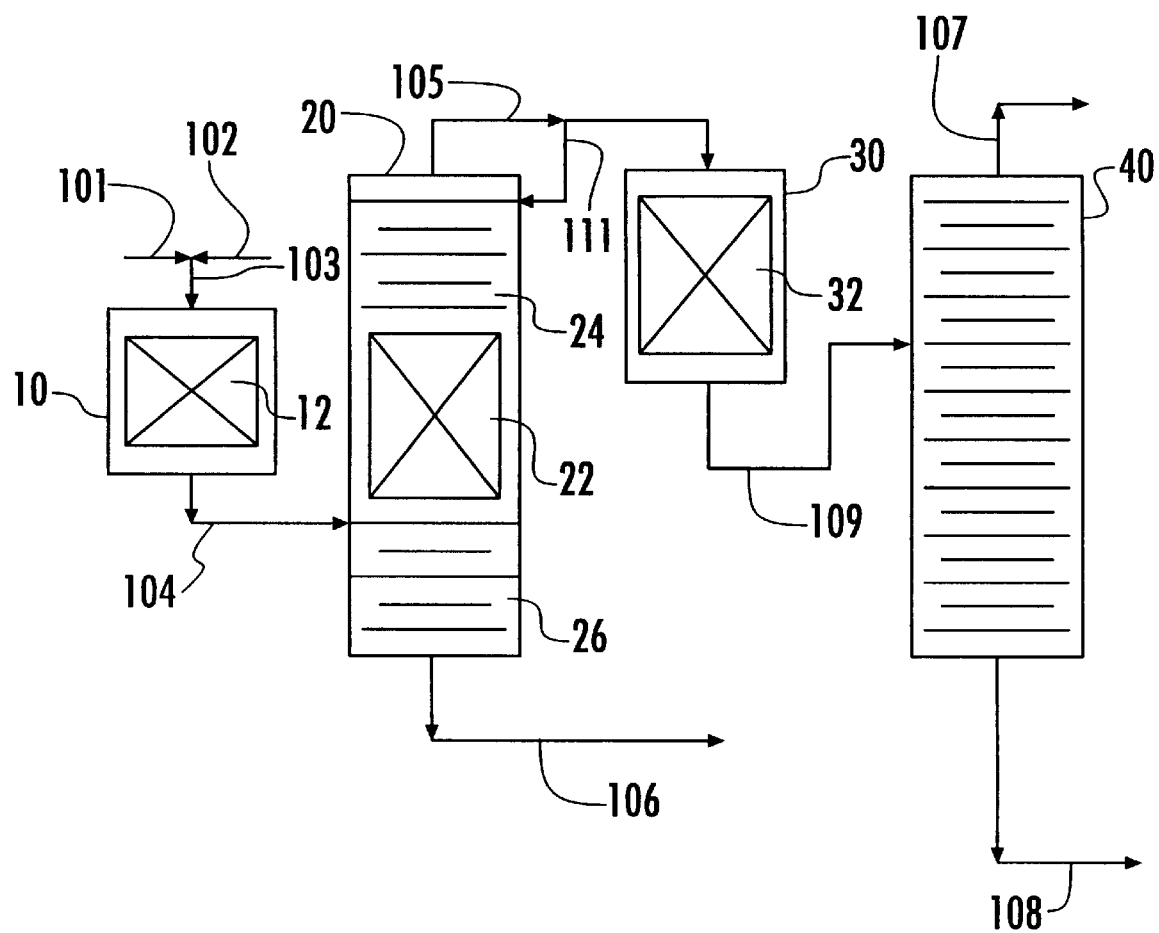
FIG. 7 is a flow diagram in schematic form of a seventh embodiment of the present invention.

Referring now to FIG. 5 a fifth embodiment of the invention is shown with which is different from that of FIG. 4 in that a reflux to the distillation column reactor 20 is provided via flow line 111 and instead of the overheads from the conventional distillation column 40 the bottoms are recycled to the distillation column reactor 20 via flow line 108. The overheads from the standard distillation column reactor contain the slip stream and are removed via flow line 107. A similar embodiment is shown in FIG. 7 except that the bottoms from the standard distillation column reactor are not recycles but simply removed as ether product via flow line 108. All of the remaining reference numerals in FIG. 5 and FIG. 7 are identical to FIG. 4.

Figure 6:
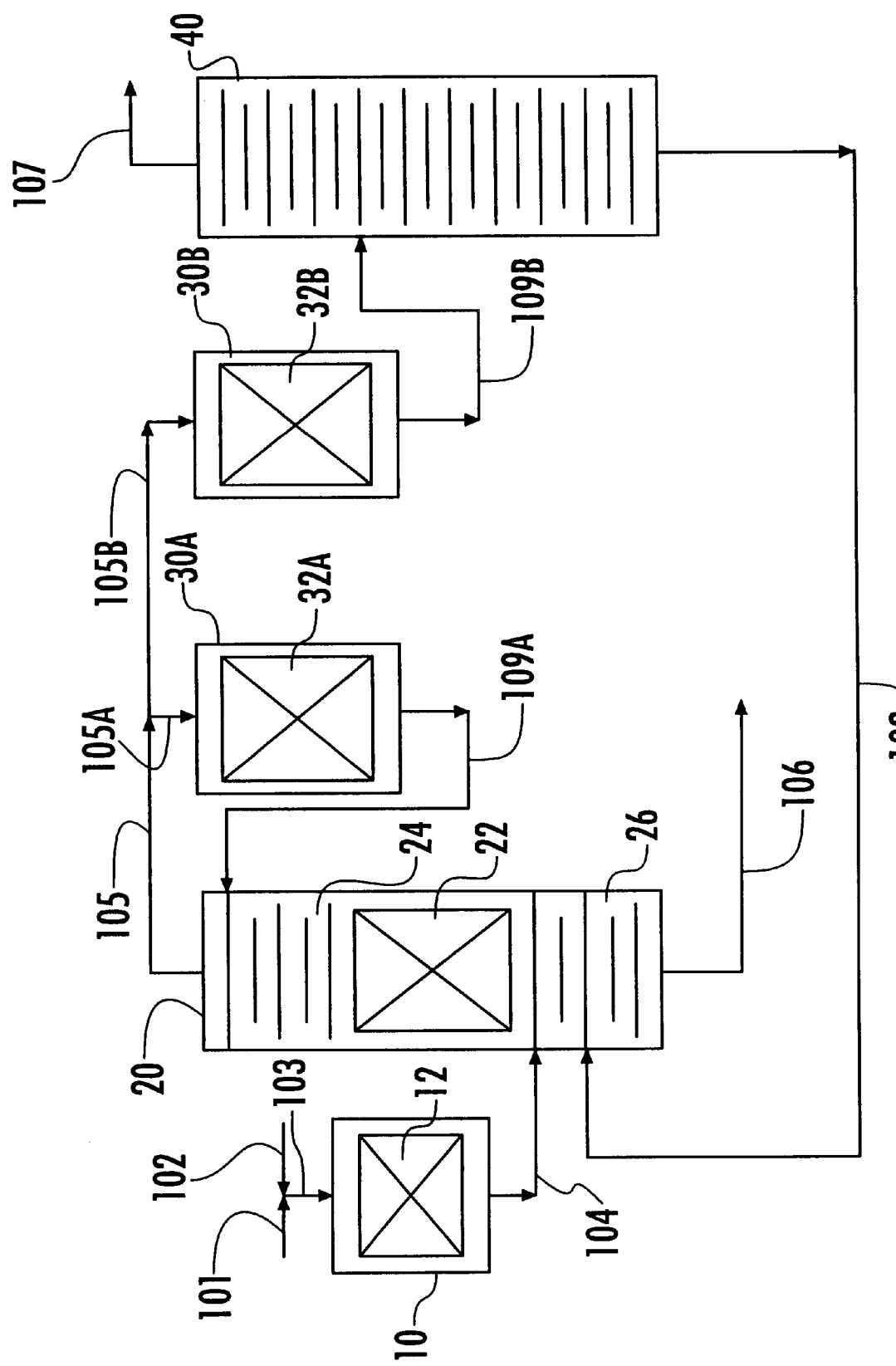
FIG. 6 is a flow diagram in schematic form of a sixth embodiment of the present invention.

Finally, there is shown another embodiment in FIG. 6 wherein the overheads from the distillation column reactor 20 are split and fed to two separate finishing reactors 30A and 30B containing catalyst beds 32A and 32B via flow lines 105A and 105B respectively. The effluent from finishing reactor 32A is returned to distillation column reactor 20 as reflux via flow line 109A. The effluent from the second finishing reactor 32B is fed to a standard distillation column 40 via flow line 109B wherein the bottoms are recycled to distillation column reactor 20 via flow line 108 and an overhead slip stream is taken via flow line 107.

While the above description has been directed to the production of MTBE by the reaction of methanol with isobutene, the process could be adapted to produce any tertiary ether utilizing other reactants.

The invention claimed is:

1. A process for the production of tertiary ethers comprising the steps of:
   (a) feeding a primary alcohol and an isoalkene to a distillation column reactor in a feed zone;

(b) concurrently in said distillation column reactor
  (i) contacting the primary alcohol and isoalkene in the presence of an etherification catalyst configured as a catalytic distillation structure in a distillation reaction zone thereby reacting a portion of the primary alcohol with a portion of the isoalkene to produce a reaction mixture containing tertiary ether product and unreacted primary alcohol and isoalkene and
  (ii) distilling the reaction mixture to separate the tertiary ether product from the unreacted primary alcohol and unreacted isoalkene;
(c) withdrawing tertiary ether product from said distillation column reactor as bottoms;
(d) withdrawing unreacted primary alcohol and unreacted isoalkene from said distillation column reactor as overheads;
(e) feeding said overheads to a single pass fixed bed reactor containing an etherification catalyst to further react primary alcohol with isoalkene to produce an effluent containing additional tertiary ether; and
(f) feeding a portion of the effluent from said single pass fixed bed reactor to said distillation column reactor.

2. The process according to claim 1 wherein said effluent is condensed and fed to said distillation column reactor as reflux.

3. The process according to claim 2 wherein a portion of said effluent is taken as a slip stream to prevent build up of inerts.

4. The process according to claim 1 wherein said effluent is fed to said distillation column reactor below said distillation reaction zone.

5. The process according to claim 4 wherein a portion of said overhead is taken as a slip stream to prevent build up of inerts.

6. The process according to claim 1 wherein a portion of said effluent is condensed and fed to said distillation column as reflux and a portion is fed to said distillation column reactor below said distillation reaction zone.

7. The process according to claim 6 wherein a portion of said effluent is taken as a slip stream to prevent build up of inerts.

8. The process according to claim 1 wherein a portion of said overheads is condensed and returned to said distillation column reactor as reflux.

9. The process according to claim 8 wherein a portion of said overheads is taken as a slip stream to prevent build up of inerts.

10. The process according to claim 1 wherein a portion of said overheads is fed to a second single pass fixed bed reactor containing an etherification catalyst to further react primary alcohol with isoalkene to produce a second effluent containing additional tertiary ether and wherein said second effluent is fed to a standard distillation column for separation of ether as bottoms from unreacted material as overheads.

11. The process according to claim 10 wherein the bottoms from said standard distillation column reactor is fed to said distillation column reactor.

12. The process according to claim 1 wherein a portion of the overheads from said standard distillation column are condensed and returned to said distillation column reactor as reflux.

13. A process for the production of tertiary ethers comprising the steps of:
(a) feeding a primary alcohol and an isoalkene to a distillation column reactor in a feed zone;
(b) concurrently in said distillation column reactor
  (i) contacting the primary alcohol and isoalkene in the presence of an etherification catalyst configured as a catalytic distillation structure in a distillation reaction zone thereby reacting a portion of the primary alcohol with a portion of the isoalkene to produce a reaction mixture containing tertiary ether product and unreacted primary alcohol and isoalkene and
  (ii) distilling the reaction mixture to separate the tertiary ether product from the unreacted primary alcohol and unreacted isoalkene;
(c) withdrawing tertiary ether product from said distillation column reactor as bottoms;
(d) withdrawing unreacted primary alcohol and unreacted isoalkene from said distillation column reactor as overheads;
(e) feeding said overheads to a single pass fixed bed reactor containing an etherification catalyst to further react primary alcohol with isoalkene to produce an effluent containing additional tertiary ether; and
(f) feeding the effluent from said single pass fixed bed reactor to a standard distillation column where a bottoms product containing the ether is taken and overheads product containing the unreacted alcohol is taken.

14. The process according to claim 13 wherein the bottoms from said standard distillation column reactor is fed to said distillation column reactor.

15. The process according to claim 13 wherein the overheads from said standard distillation column are condensed and returned to said distillation column reactor as reflux.

* * * * *